(12) United States Patent
Wallace et al.

(10) Patent No.: US 7,744,528 B2
(45) Date of Patent: Jun. 29, 2010

(54) METHODS AND DEVICES FOR ENDOSCOPIC IMAGING

(75) Inventors: Jeffrey M. Wallace, Charlestown, RI (US); Ananth Natarajan, San Marino, CA (US); Santosh Venkatesha, Baltimore, MD (US); Keith Peacock, Columbia, MD (US); Nitish V. Thakor, Clarksville, MD (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 1198 days.

(21) Appl. No.: 11/252,897

(22) Filed: Oct. 18, 2005

(65) Prior Publication Data

US 2006/0106283 A1 May 18, 2006

Related U.S. Application Data

(63) Continuation-in-part of application No. 10/785,802, filed on Feb. 24, 2004, now Pat. No. 7,559,890.

(60) Provisional application No. 60/450,224, filed on Feb. 26, 2003, provisional application No. 60/619,736, filed on Oct. 18, 2004.

(51) Int. Cl.
*A61B 1/00* (2006.01)
*A61B 1/04* (2006.01)
*A61B 1/06* (2006.01)
(52) U.S. Cl. ................ 600/170; 600/117
(58) Field of Classification Search ............. 600/103, 600/117, 173, 170; 382/285, 287, 289, 294–296, 382/298
See application file for complete search history.

(56) References Cited

U.S. PATENT DOCUMENTS

| 5,184,602 A | 2/1993 | Anapliotis et al. |
| 5,313,306 A | 5/1994 | Kuban et al. |
| 5,398,670 A | 3/1995 | Ortiz et al. |
| 5,764,809 A * | 6/1998 | Nomami et al. ............. 382/284 |

(Continued)

FOREIGN PATENT DOCUMENTS

JP  10-318727  12/1998

(Continued)

OTHER PUBLICATIONS

Baker et al., "A Theory of Catadioptric Image Formation", Prc. 6th Int'l Conf. on Computer Vision, Bombay, Jan. 1998, pp. 35-42.

(Continued)

*Primary Examiner*—John P Leubecker
*Assistant Examiner*—Philip R Smith
(74) *Attorney, Agent, or Firm*—Kauth, Pomeroy, Peck & Bailey LLP

(57) ABSTRACT

Embodiments include devices and methods. One embodiment includes a method for imaging an endometrial cavity, including acquiring a plurality of images using an imaging system. A first part of the imaging system is positioned within the endometrial cavity. At least portions of two or more of the images are combined into a representation of at least a portion of the endometrial cavity. The combining at least portions of two of the images may include determining any motion of the first part of the imaging system, between the two or more of the images. Other embodiments are described and claimed.

34 Claims, 21 Drawing Sheets

Single Endometrial Map

U.S. PATENT DOCUMENTS

| | | | |
|---|---|---|---|
| 5,807,237 A | 9/1998 | Tindel | |
| 5,888,193 A | 3/1999 | Breeidenthall et al. | |
| 5,961,445 A | 10/1999 | Chikama | |
| 6,248,074 B1 * | 6/2001 | Ohno et al. | 600/463 |
| 6,491,645 B1 | 12/2002 | Gaber | |
| 6,537,209 B1 | 3/2003 | Pinkhasik et al. | |
| 6,591,130 B2 * | 7/2003 | Shahidi | 600/424 |
| 6,638,216 B1 | 10/2003 | Durell | |
| 6,668,185 B2 | 12/2003 | Toida | |
| 6,751,494 B2 * | 6/2004 | Collier et al. | 600/407 |
| 6,809,729 B2 * | 10/2004 | Greasley | 345/426 |
| 6,887,196 B2 | 5/2005 | Arai et al. | |
| 6,929,603 B2 | 8/2005 | Durell | |
| 6,980,690 B1 * | 12/2005 | Taylor et al. | 382/154 |
| 7,110,124 B2 | 9/2006 | Jensen et al. | |
| 2002/0052547 A1 * | 5/2002 | Toida | 600/425 |
| 2003/0095338 A1 * | 5/2003 | Singh et al. | 359/725 |
| 2003/0191369 A1 | 10/2003 | Arai et al. | |
| 2004/0122327 A1 | 6/2004 | Belson et al. | |
| 2004/0254424 A1 | 12/2004 | Simkulet et al. | |
| 2005/0182295 A1 * | 8/2005 | Soper et al. | 600/117 |
| 2005/0228275 A1 * | 10/2005 | Kawashima | 600/437 |

FOREIGN PATENT DOCUMENTS

| | | |
|---|---|---|
| JP | 11-174603 | 7/1999 |

OTHER PUBLICATIONS

Nayar, "Omnidirectional Video Camera", Proc. DARPA Image Understanding Workshop, New Orleans, May 1997.

Svoboda et al., "Central Panoramic Cameras: Geometry and Design", Center for Machine Perception Czech Technical University Research Report No. K335/97/147, Dec. 5, 1997.

* cited by examiner

Single Endometrial Map

METHODS AND DEVICES FOR ENDOSCOPIC IMAGING

This application is a continuation-in-part of U.S. application Ser. No. 10/785,802, filed Feb. 24, 2004, now U.S. Pat No. 7,559,890 which claims priority in U.S. Provisional Application No. 60/450,224, filed Feb. 26, 2003; and this continuation-in-part application claims priority in U.S. Provisional Application No. 60/619,736, filed on Oct. 18, 2004. The content of each application number listed above is hereby incorporated by reference in its entirety.

RELATED ART

Many types of imaging, include endoscopy, are based on the visual inspection of a live or stored 2-D visual image. This live or stored 2-D visual image inspection may not yield adequate information for detailed evaluation. This shortcoming is present in a number of different fields of medicine, including, but not limited to, gynecology.

A common practice in gynecology is for a woman to have an annual examination including speculum and bimanual examination and a Papanicolau smear (which primarily screens for cervical cancer). On the other hand, there is no current screening test for endometrial cancer, the most prevalent form of gynecological cancer. Therefore, imaging and biopsy is usually delayed until after symptoms develop. Patients with endometrial carcinoma or hyperplasia typically exhibit increased or irregular menses or postmenopausal vaginal bleeding (PMB). The standard of care as recommended by the American College of Obstetricians and Gynecologists is for patients with these symptoms to undergo office-based endometrial biopsy (EMB) and endocervical curettage (ECC). The EMB is a blind biopsy done typically with an endometrial Pipelle™. The Pipelle™ is a disposable plastic tube measuring 3.1 mm in diameter with an internal plunger which is drawn back to create a small amount of suction once the device has been introduced into the endometrial cavity via the cervix. By moving the device in and out, a sample of endometrial tissue is removed for histologic examination.

None of the above techniques use imaging of the endometrium. There are currently two imaging modalities that are available. The first is transvaginal ultrasound, which may be useful in screening patients with PMB for endometrial cancer. The other technique for imaging the endometrium is hysteroscopy. Using the hysteroscope for image-guided biopsy has been shown to be superior to the above blind procedures. However, the majority of gynecologists do not perform hysteroscopy. Beyond the issues of pain, invasiveness, and morbidity, there is a steep learning curve. In addition, the use of a distending media, for example, saline or a gas (e.g., $CO_2$) to create open space in the uterus may lead to problems. In addition, because the hysteroscope can only image the tissue in front of it, experience and manual dexterity are required in order to examine the whole endometrium.

BRIEF DESCRIPTION OF THE DRAWINGS

Certain embodiments of the invention are described with reference to the accompanying drawings, which, for illustrative purposes, are not necessarily drawn to scale.

DETAILED DESCRIPTION

Figure 1:
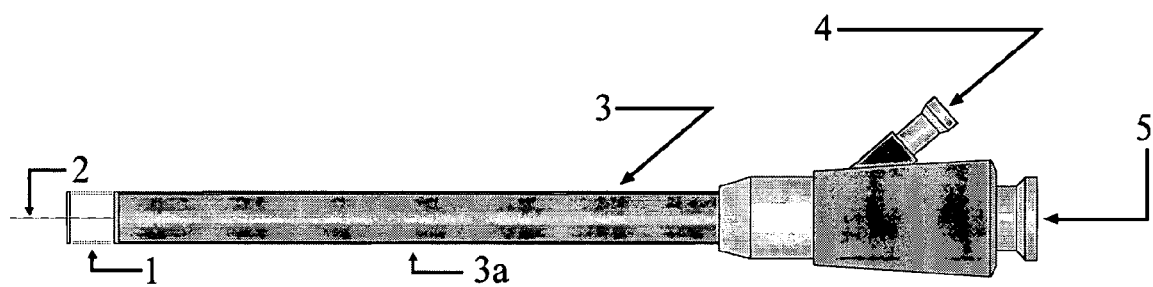
FIG. 1 is a schematic of an embodiment of an imaging apparatus that allows for omni-directional viewing. Light is collected at the omni-directional tip (1) and is transferred to the imaging channel (5) with the appropriate detector.

As described above, the visual inspection of a live or stored 2-D visual image may not provide sufficient information for a detailed evaluation. Such visual inspection does not involve the incorporation of additionally data from other dimensions, such as images acquired at other instances in time, images which use alternate modalities, or images at other depths (3-D images above and below the surface of the tissue). It does not incorporate physiological data such as blood flow or evidence of pathology.

Certain embodiments of the present invention may pertain to minimally invasive imaging systems and methods used to identify or diagnose pathology of an organ system cavity and/or provide guidance for imaging guided procedures, including but not limited to biopsy and therapy delivery. Such organ system cavities may include, but are not limited to, an endometrial cavity, a gastrointestinal lumen, an orthopedic cavity, an orthopedic joint cavity, a sinus cavity, a nasal passageway, an ear canal, an oral cavity, an intracranial space, a portion of the lung cavity, a bladder cavity, a cavity within the heart, a cavity within the vascular system, or a portion of a thoracic cavity. Certain embodiments of the present invention may include the use of a minimally invasive imaging system to image an organ system cavity, which may include the space within the cavity's lumen, the tissue that lines the cavity, and the tissue that is in proximity to the tissue that lines the cavity. In certain preferred embodiments, endometrial imaging is described. The endometrial cavity may include the endometrial lining and/or underlying tissue or pathology residing above and/or below the surface of the endometrial cavity including, but not limited to the mucosa, the sub-mucosa, sub-surface endometrial tissue, the myometrium layers, and the endocervical canal.

One embodiment of a minimally invasive imaging system includes, but is not limited to, an endoscope, a light source, a cable to connect the light source to the endoscope, an imaging device that may be coupled to the endoscope, a computer system, a cable connecting the imaging device to the computer system, and data processing software stored in the memory of the computer system.

In certain embodiments, an endoscope may be positioned and moved manually by a user throughout at least a portion of an organ system cavity while images of the cavity are being captured by an imaging device. Certain embodiments may also include an imaging system with an endoscope that is fixated to a mechanical fixture which may allow the endoscope to move in certain degrees of freedom, including, but not limited to, a linear scale or servomotor track, such that the endoscope may move throughout at least a portion of the organ system cavity and may capture images of the cavity with an imaging device. Certain embodiments may also include imaging devices such as, for example, full color CCD, spectral multi-wavelength imaging technology (including, but not limited to, ultraviolet, visible, near infrared, and infrared light), OCD devices (optical coherence tomography), spectroscopy devices, or other electrical transducers (including, but not limited to, ultrasound transducers, radiation sensor transducers, and nuclear medicine sensor transducers), to produce one or more detailed images of the endometrial cavity including, but not limited to, up to and including 360-degree panoramic images.

Certain embodiments of the invention may include the use of one or more imaging modalities either independently or in combination. Certain embodiments of the invention may include, but are not limited to, the use of at least two systems of the same imaging modality, the use of at least two systems of different imaging modalities, or a combination of systems, which may be of the same imaging modality or different imaging modalities. Examples may include, but are not limited to, the use of multiple endoscopes, the use of multiple selected light wavelength imaging systems, the use of endoscopy with one or more imaging systems that may incorporate an electrical transducer, and the use of one or more imaging systems that may incorporate electrical transducers. Certain embodiments of the present invention may include the use of stereo imaging. In such embodiments, imaging systems may include, but are not limited to, stereo endoscopes, as a type of imaging modality.

Certain embodiments of the invention include the use of software or computational methods to calculate or model the motion that the imaging system has undertaken between two or more image captures, which is an example of visual motion tracking. Certain embodiments of the present invention use tracking methods that may include, but are not limited to, image processing, contact trackers (including, but not limited to physical frames and physical stages), non-contact trackers (including, but not limited to, electromagnetic trackers, optical trackers, non-contact trackers, and global positioning system trackers), to calculate or model the motion that an imaging system may have undertaken between two or more image captures. Certain embodiments of the present invention may incorporate the use of one or more calibration processes to improve the system's performance, for example, calibrations processes for tracking methods (including, but not limited to visual motion tracking).

Certain embodiments also can have the ability to combine a series of one or more images or a subset of that series by calculating the motion that occurred between one or more images, and then 'stitching' or combining all or portions of the images together in a combined or collaged images. Certain embodiments may include combining images in one or more image series or one or more subsets of one or more images series to create a representation of the organ system cavity or portion thereof. Such embodiments may include the use of a stereo imaging modality, such as, but not limited to, stereo endoscopy, to create a representation of the organ system cavity or portion thereof, wherein the representation may include at least three dimensional features, such as, but not limited to, visualizing depth or a form of depth perception. The process of combining images is an example of image collaging.

Certain embodiments of the present invention may combine a series of one or more images or a subset of that series into at least a two dimensional representation of an organ system cavity or a portion of the organ system cavity being imaged. This may include, but is not limited to, computing and/or measuring an organ system cavity's or a portion of an organ system cavity's three dimensional structure and creating a representation of the organ system cavity or portion of the organ system cavity. Certain embodiments of the present invention may include the combination of a series of images or a subset of a series of images, where the series of images may include images originating from one or more imaging modalities. Such embodiments may combine images of multiple image modalities (multi-modal images) into a representation of 2 or more dimensions. In certain embodiments that may combine images from multiple modalities, the resulting representation may be visualized in a plurality of methods, including, but not limited to, overlaying more than one image on top of the other, (where one or more of the images may be partially transparent), or changing the color or presentation of one of more images based on the data contain in one or more other images. Certain embodiments of the present invention may include the use of multi-modal imaging. Certain embodiments of the present invention may include the use or reference of one type of imaging in order to assist or guide the combination of images of one or more imaging modalities. Embodiments of the invention may utilize visual motion tracking to process one or more images taken within a cavity and begin to combine images or portion of images together into one or more collaged images. In certain embodiments of the present invention, the motion tracking and/or the combination of images that may create a representation of the tissue or subject that may be images may be accomplished in realtime (including, but not limited to, during image capture), offline (including, but not limited to, after image capture), or a combination of both. Certain embodiments of the present invention may utilize the combined images, a portion of the combined images, or a representation of a portion of the combined images as a tool to identify or diagnose pathology within an organ system cavity. Certain embodiments of the present invention may utilized the combined images, a portion of the combined images, or a representation of a portion of the combined images as guidance for an image-guided procedures, including, but not limited to, biopsy or therapy delivery. Certain embodiments of the present invention may utilize the combined images or a portion of the combined images, or a representation of the combined images as guidance to allow a user or tool to return to a portion of the combined image or portion of the combined image or representation of the combined image. This may include returning to a portion that the user or tool had previously established or attended to. Such embodiments may include the use of computer controlled return or the use of computer guidance to assist a user to return to a portion of the combined image or a portion of a representation of the combined images.

Certain embodiments of the present invention include the capture of multiple images. Some embodiments may capture multiple images from the same perspective or the same angle. In such embodiments, the embodies system utilize the captured images or portions of the captured images to remove noise or artifacts from the combined representation. Certain embodiments of the invention may capture multiple images from a plurality of angles. In such embodiments, the embodied system may utilized the captured images to calculate, compute, or model three dimensional information related to the tissue or subject that may be imaged. Such information, or a subset of such information may be useful for creating representation contain three dimensional features.

Certain embodiments of the present invention may utilize the captured images or portions of the captured images or representations of the captured images to measure, monitor, compute, or model temporal or time-varying elements or aspects of the tissue or subject that may be imaged. In certain embodied systems, by comparing the captured images or portions of the captured images or representation of the captured images at difference instances in time, variations or changes that may have occurred may be realized. Embodiments may include imaging before and after a targeted or non-targeted therapy was applied and the embodied system may be able to measure, monitor, compute, or model the change or changes that may have resulted from therapy.

In accordance with certain embodiments, in order to image the tissue within the endometrial cavity (or organ cavity), a specialized endoscope is used. As seen in the embodiment illustrated in FIG. 1, an imaging apparatus includes a rigid or flexible endoscope (3), an illumination channel (4), and an imaging channel (5). A camera, electrical transducer or other imaging technology may be attached to the imaging channel (5) to capture images. The endoscope contains a body portion (3a) that surrounds at least a portion of the imaging channel of the device. One aspect of the imaging apparatus of this embodiment is the omni-directional tip (1) that will allow it to visualize 360 degrees of the endometrial cavity perpendicular or near perpendicular to the optical axis (2) at a position in the endometrium at or adjacent to the tip. The omni-directional tip may also be positioned a distance away from an end region of the endoscope. The endoscope is preferably positioned transcervically to the uterine fundus. As the apparatus is introduced or retracted, images of the endometrial cavity can be captured as the tip of the scope passes through the cavity.

Figure 2:
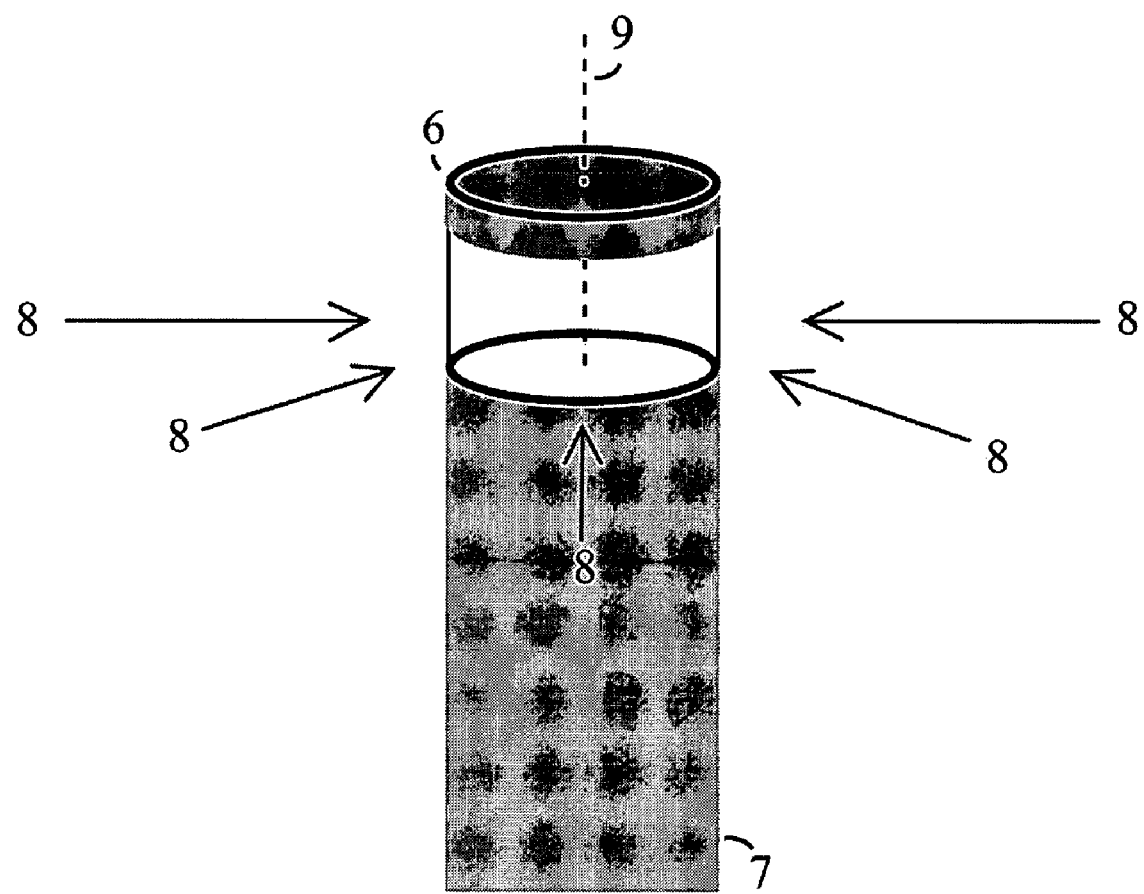
FIG. 2 is an illustration of an embodiment of an omni-directional tip (6) collecting light from all directions. Light (8) entering the tip will be transferred into the endoscope body portion (7).

As seen in FIG. 2, any light (8) collected at the omnidirectional tip (6) will be imaged into the endoscope body portion (7) and transferred to an imaging sensor on the other end of the endoscope. To illuminate the field of view, fiber optics may be used. Fiber optic light conductors may be mounted coaxially around the image channel of the endoscope, much like standard endoscopes. This allows for transmission of light from an illumination channel (see FIG. 1 illumination channel 4) to the omni-directional tip, where the light can be directed to the field of view and therefore illuminate the tissue that will be imaged. Unlike some conventional imaging methods in which imaging is done in front of the endoscope tip with a limited field of view using liquid or gas distention, (as done in conventional hysteroscopy and related imaging), certain embodiments image the endometrial cavity coapted 360 degrees around the tip, perpendicular or near perpendicular to the optical axis (2). Such device will capture the images of tissue and collect a panoramic view (360 degree view). When the endoscope is retracted/inserted through the cavity, as described below (FIG. 8), the successive views that are formed can be combined into a collage of all the images. Therefore a full image of all the views can be combined displaying the entire length of the endometrial cavity.

Figure 3:
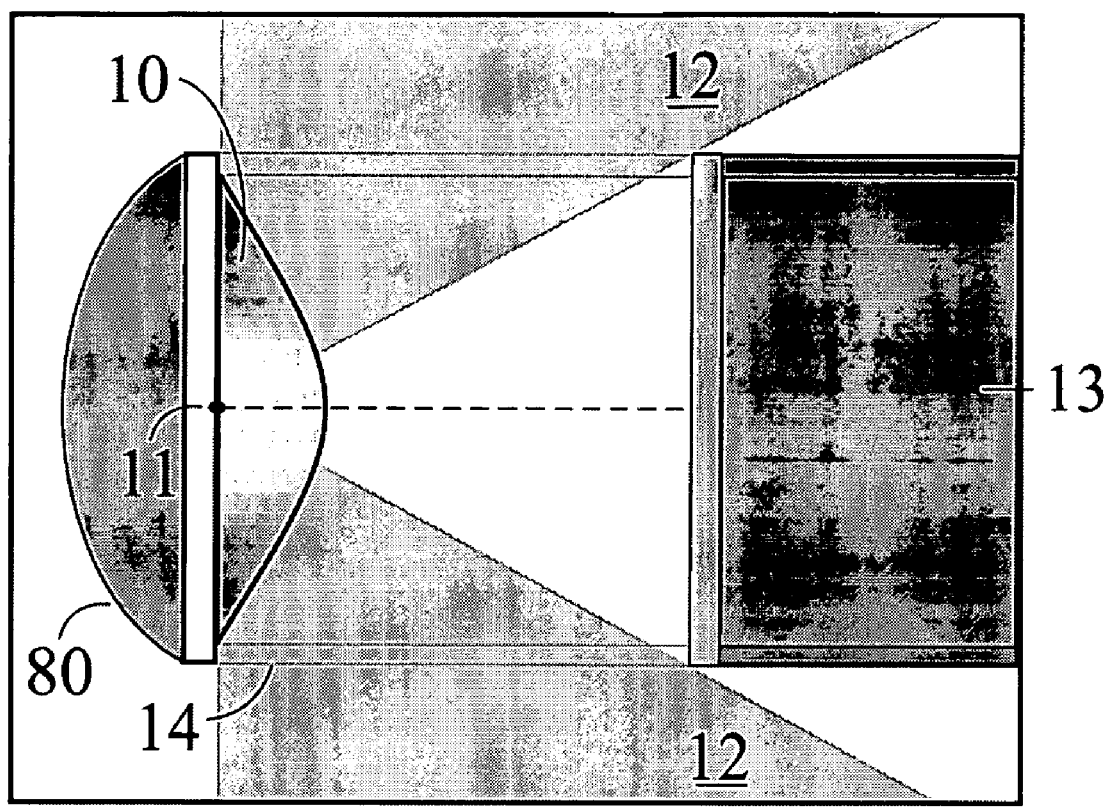
FIG. 3 is a schematic of an embodiment of an omni-directional tip. Using a reflecting medium, such as a mirror, the light within the displayed field of view (12) aimed at the perspective point (11) will be reflected off of the tip (10) and imaged through the endoscope (13).
Figure 13:
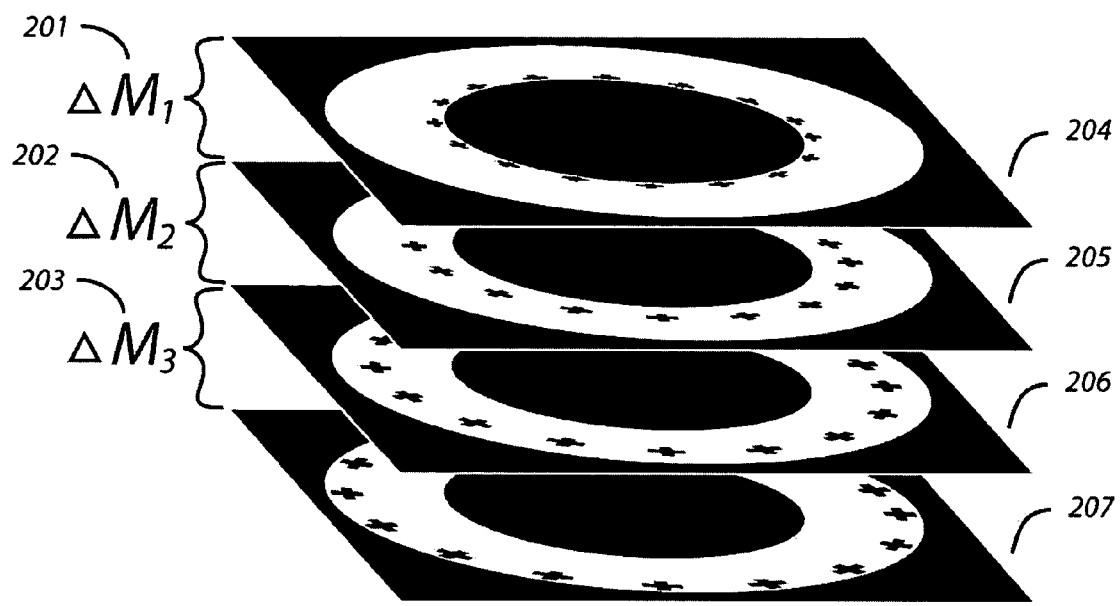
FIG. 13 is a schematic including a captured image series in accordance with certain embodiments. In between each image capture, the imaging system may have undergone some motion (in the shown embodiment, this is represented by, but not limited to $\Delta Z_n$). Other embodiments can contain more complex motion, including but not limited to rotation, scaling, deformation, patient motion, or motion caused by hand tremor.
Figure 14:
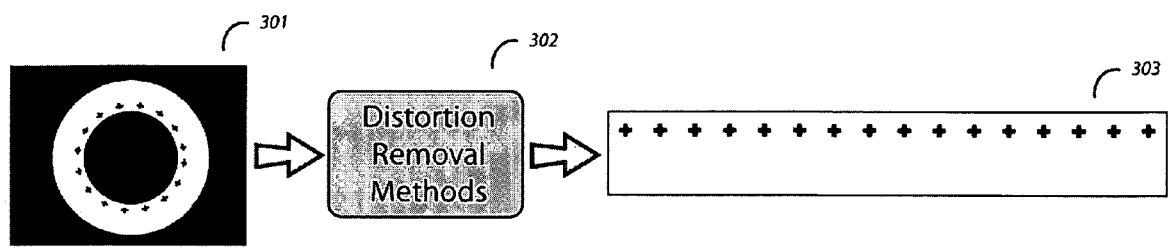
FIG. 14 illustrates unwarping the captured images and/or taking out the distortion within the images in accordance with certain embodiments.

The ability of the imaging apparatus to capture light from 360 degrees at the omni-directional tip is illustrated in multiple embodiments. FIG. 13 shows a schematic of one embodiment of an omni-directional tip. This method includes an omni-directional tip that uses a reflective element (10), such as a mirror to image the surrounding tissue. The shape of the reflective element used in this embodiment can vary depending on the subsequent image processing that will be used to un-warp the collected image. Any light within the field of view (12) that can create an image will pass through a window (14) on the tip. The window (14) may preferably made from a clear material such as plastic, acrylic, glass or some other clear substance. The image is reflected into the endoscope body portion (13) to be imaged by a sensor at the imaging mount of the endoscope (See imaging mount 5 in FIG. 1). An optional element can be attached to the tip of the endoscope. An example of such an element is an end cap structure (80). The end cap structure may take a variety of shapes, for example a convex shape such as that shown in end cap (80) in FIG. 3. Such an end cap may facilitate insertion and removal of the endoscope. Through this embodiment, the imaging tip will collect images of tissue that are within the field of view (12)—tissue which is 90 degrees with respect to the optical axis, and further behind the tip. FIG. 14 illustrates the embodiment further. Any light originating within the endoscope's field of view (12), will be reflected off the reflective element (10), and transferred through the endoscope to the imaging detector.

Figure 4:
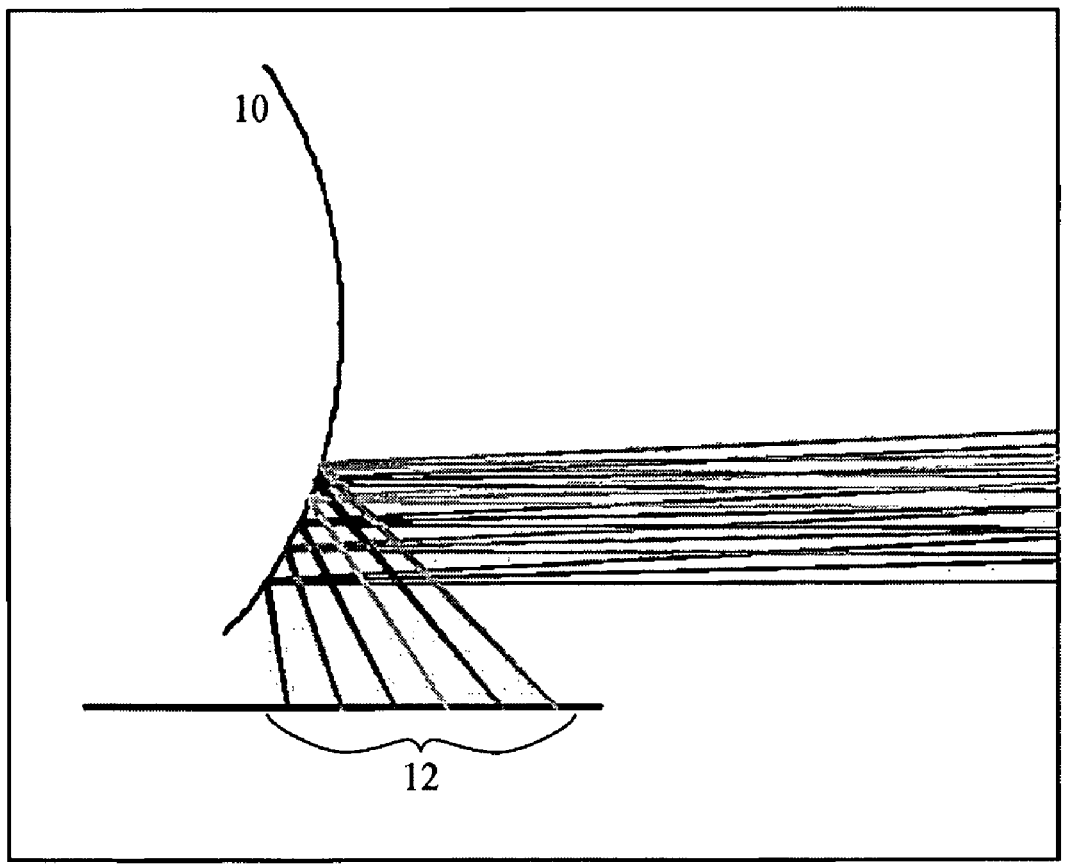
FIG. 4 illustrates how light is reflected off a reflective surface in the field of view in accordance with an embodiment of the present invention. Any object within the field of view (12) will project light off the mirror or other reflective surface (10) into the image transfer optics of the endoscope.
Figure 5:
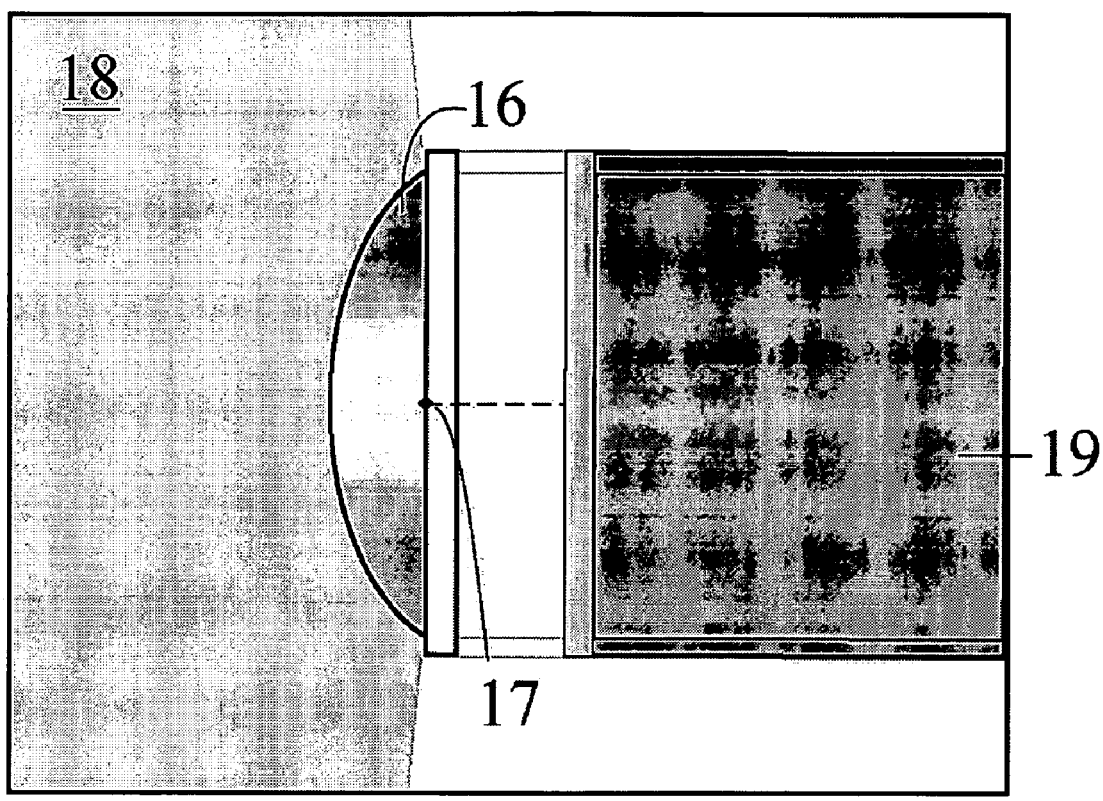
FIG. 5 is a schematic of another embodiment of an omni-directional tip. By refracting the light through the use of a lens element (16), light within the field of view (18) aimed at the perspective point (17) is captured into the endoscope (19).
Figure 16:
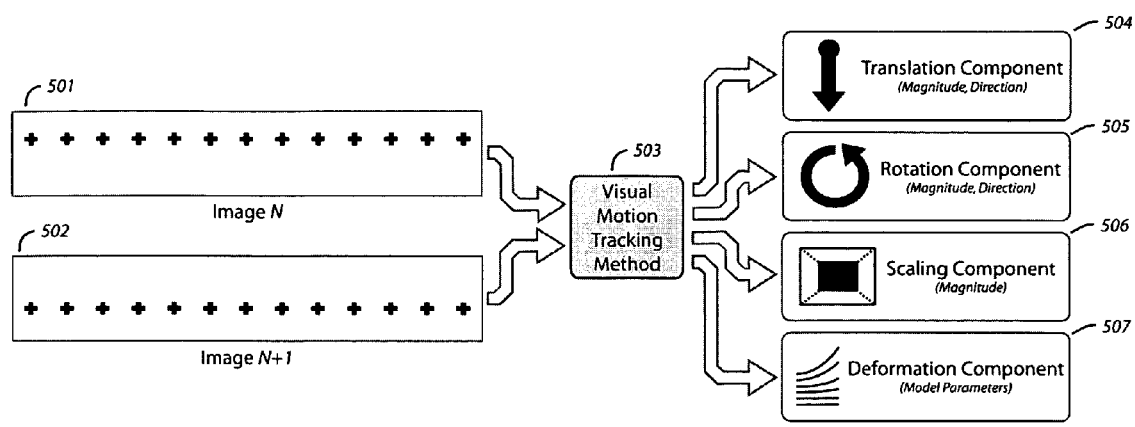
FIG. 16 illustrates a visual motion tracking system in accordance with certain embodiments. The illustrated motion tracking method may input two or more images in an image series and compute the motion that has occurred between imaging.

Another embodiment of an omni-directional tip is shown in FIG. 16. Instead of a reflective element as before, this embodiment uses a lens or a system of lenses (16) to refract the light into the endoscope. All the light that can form an image within the field of view (18) will be refracted into the endoscope body portion (19) and transferred to the imaging sensor at the imaging mount of the endoscope. Using a lens element (16), this embodiment captures images of tissue within the field of view (18) that differs from the field of view (12) in the embodiment illustrated in FIGS. 3 & 4. In the embodiment illustrated in FIG. 5, the field of view (18) includes tissue that is in front and tissue that is oriented up to 90 degrees with respect to the optical axis. As seen in the embodiments in FIGS. 3 and 5, at least a portion of the field of view ((12) in FIG. 3 and (18) in FIG. 5) extends around a circumference of a portion of the endoscope and thus an image including tissue extending around a circumference of the endoscope may be obtained.

Figure 6:
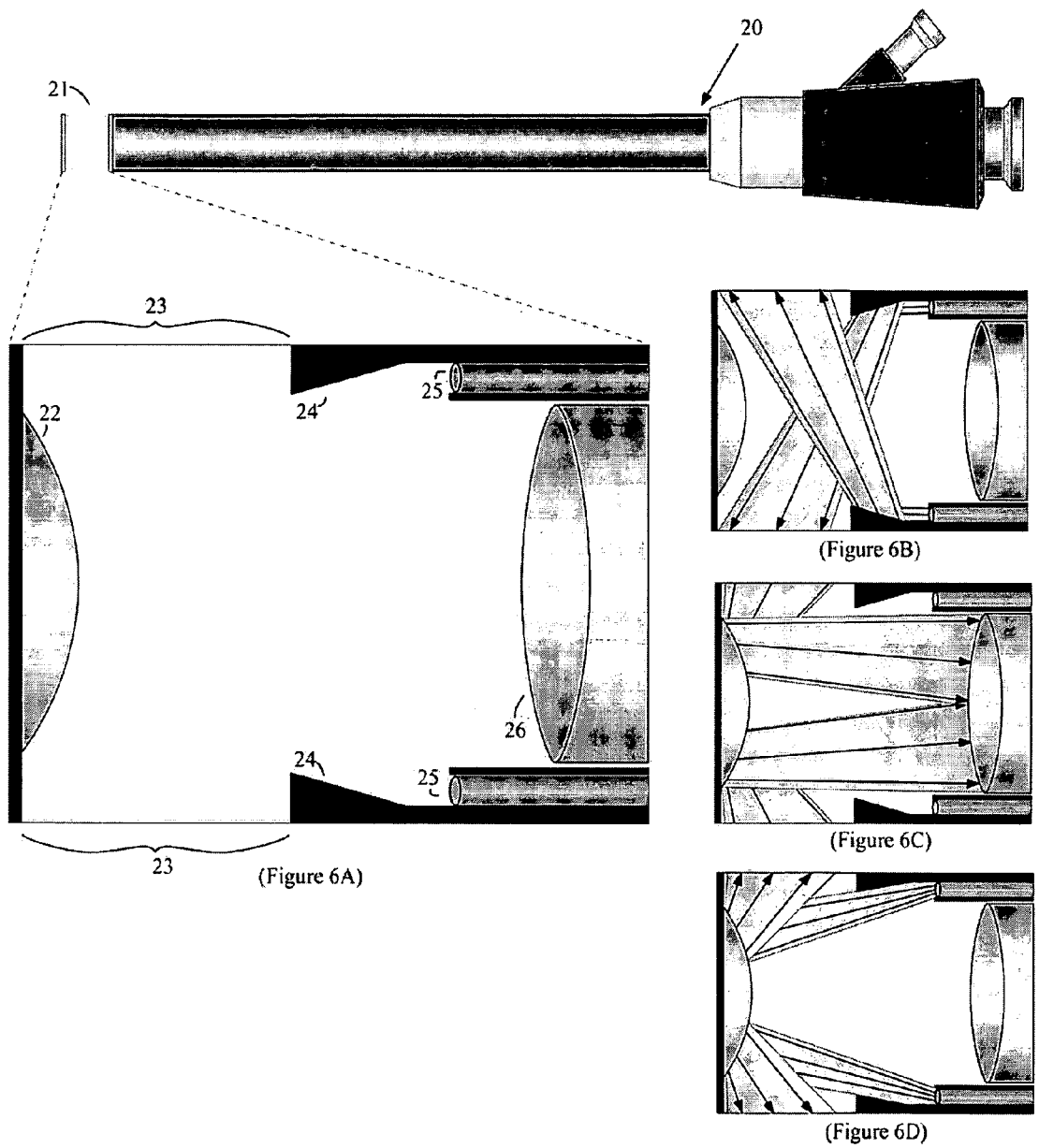
FIGS. 6(a)-(d) illustrate embodiments of an illumination system in coordination with a reflective element imaging system.
Figure 19:
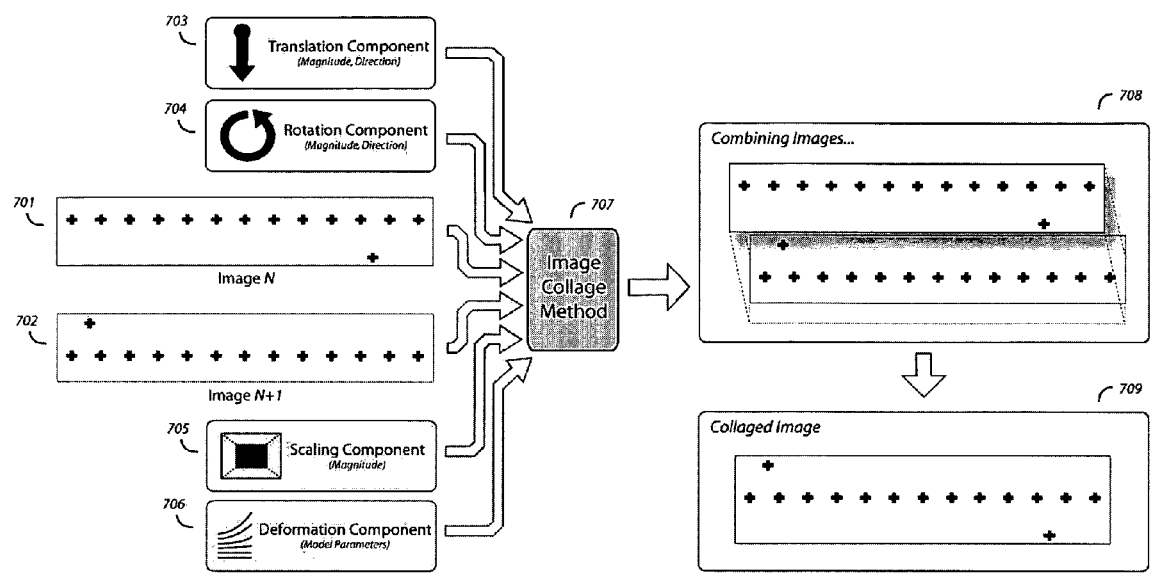
FIG. 19 illustrates using the information about the interframe motion (the motion occurring between two image captures) and combining portions or all the images (defined as collaging) into a single image in accordance with certain embodiments. This process may be iterated with more than two images in an image series or subset of an image series to create on or more collaged images.

By combining the omni-directional tip with a method for illuminating the field of view from the illumination brought in by the fiber optics mounted coaxially around the endoscope, an embodiment of the imaging system can be established. FIG. 19 illustrates an embodiment of the invention using a reflective element to illuminate the field and a reflective element to image the field. This embodiment includes a more detailed view of an omni-directional tip (21) including a reflective element (22) similar to the reflective element (10) illustrated in FIG. 3. Looking at a cross section of the endoscope's (20) omni-directional tip (21) and region adjacent thereto in the blown up portion of FIG. 6, this embodiment uses fiber optics (25) that are mounted coaxially around imaging optics (26) to illuminate the field of view (23). Light passing through the fiber optics (25), will reflect off a reflecting element, such as a mirror (24) to illuminate the field of view (23) by crossing the optical axis, as illustrated in FIG. 6(b), which shows a general schematic of this embodiment illustrating a methodology of illuminating the field of view (23). In parallel with this, as illustrated in FIG. 6(c), the imaging system collects light (indicated by lines and arrows) from the field of view (23) and delivers the light towards the endoscope optics (26). An alternate embodiment of the system is shown in FIG. 6D. This embodiment uses the illumination coming from the coaxial fiber optics (25) and reflects the light off the imaging mirror (22) to illuminate the field of view (23). In both embodiments, through the use of the endoscope optics (26), the image is transferred to a detector connected at the end of the imaging channel (5). Non-uniform illumination that may be caused by fiber optic illuminators that are mounted coaxially around the endoscope is corrected subsequently by software once the image acquisition has been completed.

Figure 20:
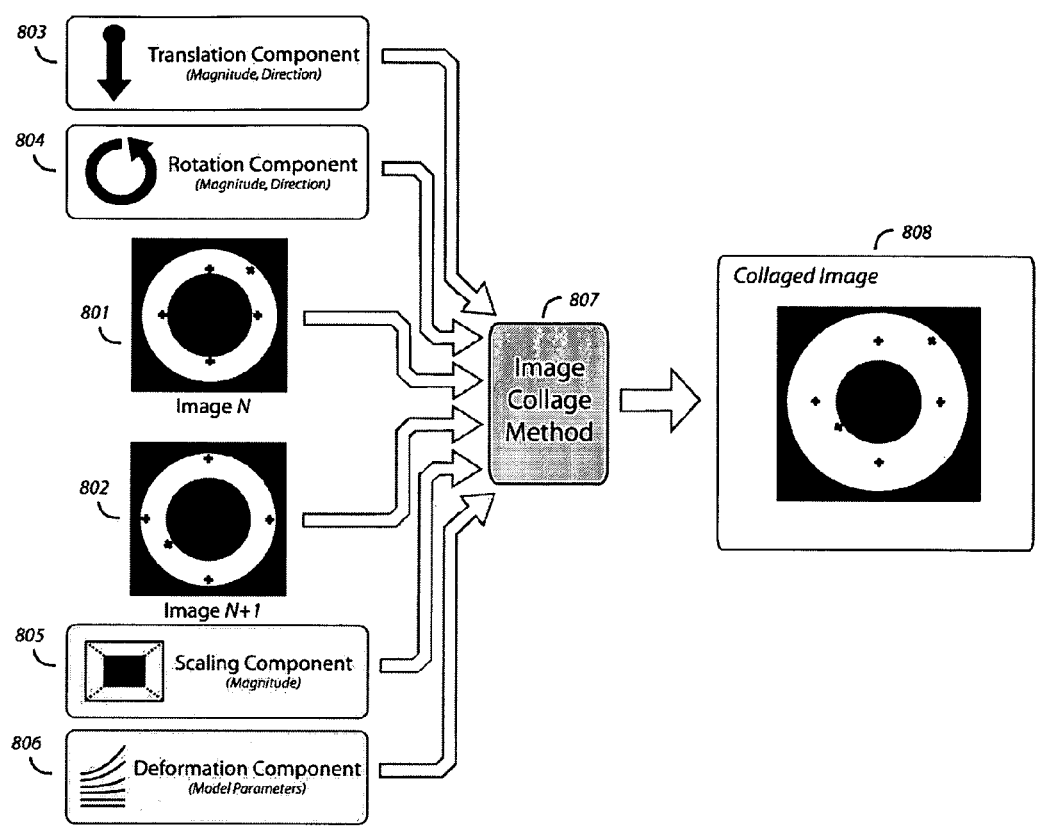
FIG. 20 illustrates an image collaging system in accordance with certain embodiments. This system utilizes images that may not have undergone distortion removal or unwarping.

An example of the operation of an imaging apparatus in accordance with a preferred embodiment of the present invention is demonstrated in FIG. 20. A systematic method for tracking the position of the endoscope tip is used in this embodiment. This can be accomplished by a position sensor. The position sensor (38) and the controller (39) will control or track the position of the preferably rigid endoscope body portion (29) with the omni-directional tip (30) in order to capture information from endometrial cavity (31). Therefore, as each image is captured in order to use each image to describe a portion of the endometrium, the physical location of the tissue imaged in each capture will be monitored. The omni-directional viewing tip (30) is positioned to image the tissue. Illumination generated by a light source (32) is inputted into the apparatus's illumination channel (33) on the endoscope. The illumination travels through the endoscope and illuminate the field of view through either the omni-directional tip (30) or another reflective or refractive element. The light reflects off the endometrial cavity (31) that is surrounding the tip and be collected back into the endoscope's imaging channel (34) through use of the omni-directional tip. The output of the imaging channel (34) travels to the imaging sensor (35) that is mounted on the endoscope. Digital images of the light is captured with the use of the imaging sensor (35) and computer (36) and its relevant image acquisition. The images that are captured are stored on the computer (36) for processing and displayed on a monitor (37) for observation by the user after the processing is complete. Embodiments may also include one or more lenses (85) positioned at various locations within the body portion (29) of the endoscope.

By positioning filtering elements within the optical path of the embodiment, specific wavelengths of light are imaged. Through the use of wavelength specific imaging, functional information about tissue physiology can be captured. A number of embodiments of this are shown within FIG. 20. A first method can be visualized by placing a filtering element at position (41) where the illumination light is limited to a specific bandwidth determined by the filtering element. Therefore all the light that illuminates the field of view is filtered and the light that is imaged through the imaging channel (34) is of specific wavelengths. A second method can be accomplished if a filtering element is placed at location (40). The tissue is illuminated with broadband light from the light source (32), and the light coming back through the imaging channel (34) is not limited. However, the filtering element at position (40) filters the light just before it is imaged by the imager (35). Therefore, only light of a particular wavelength is captured. Using either method, the filtering element allows for selective imaging of light. In addition, certain embodiments may utilize filters at both locations 40 and 41 or even at different locations if desired. By selecting the correct filter characteristics and location(s), any light, whether in the ultra-violet, visible or infrared spectrum, can be imaged.

Figure 7:
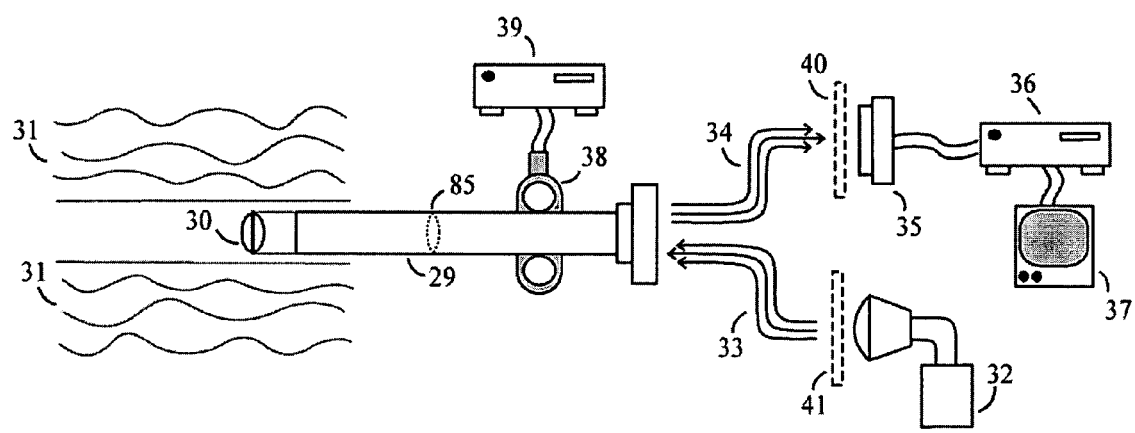
FIG. 7 shows an illustration of how an embodiment of the apparatus may capture images of the endometrial cavity. The endoscope (29) is attached to a position sensor (38). By changing the position of the endoscope, with the position sensor, the imager (35) will be exposed to different areas of the endometrial cavity (31). Through this means, in a systematic fashion, all areas along the length of the cavity may be captured.
Figure 8:
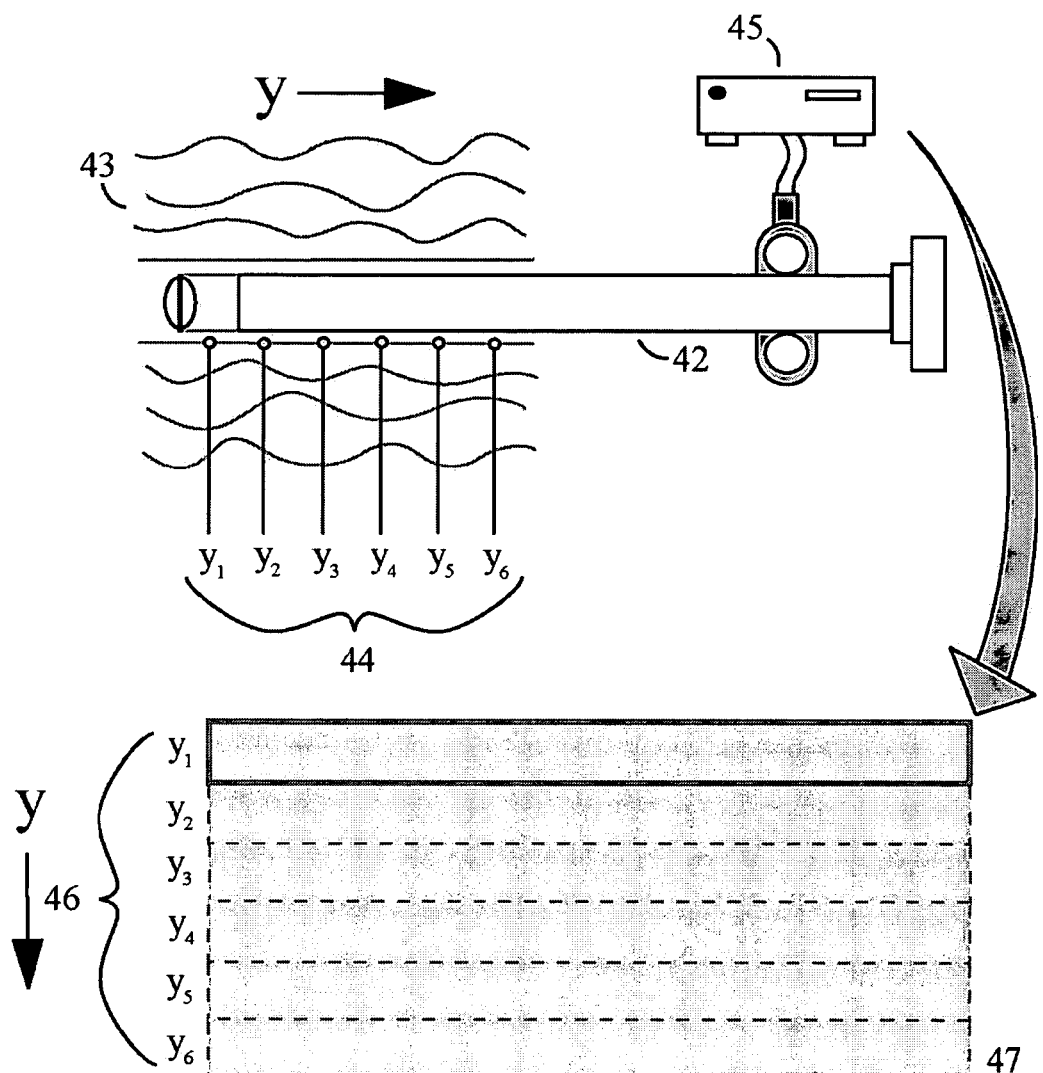
FIG. 8 shows a preferred embodiment of an image collection process. The endoscope (42) will transverse through the endometrial cavity (43) through several positions (44). Through the use of the position sensor setup (45), the positions within the endometrial cavity (43) will correspond to segments (46) of the complete single endometrial map (47).

FIG. 8 illustrates a method embodiment for imaging the entire endometrial cavity using the endoscope such as that illustrated in FIG. 7. Once the endoscope tip (30) is in position within the endometrial cavity (31), it can begin image acquisition. After an image is captured at one location, through the use of the position sensor (38) and controller (39), the endoscope tip (30) will be repositioned to the next position within the cavity. An image is captured at the new location and the endoscope is moved again. As the endoscope tip (30) moves through all the positions $y_1, y_2, \ldots$ (44), it will capture all the images in series. Once all images have been captured, the image acquisition computer will perform image processing on the collected images to generate a single 2-dimensional map of the imaged region (47). The positioning sensor system (45) keeps track of all positions that the imaging apparatus acquired and maintains a single coordinate system for the 2-dimensional map. This allows the position sensor to translate any position (46) on the 2-dimensional map to a position (44) within the endometrial cavity (43). This allows a user the ability to select an area of concern and then return to that location for biopsy.

Figure 9:
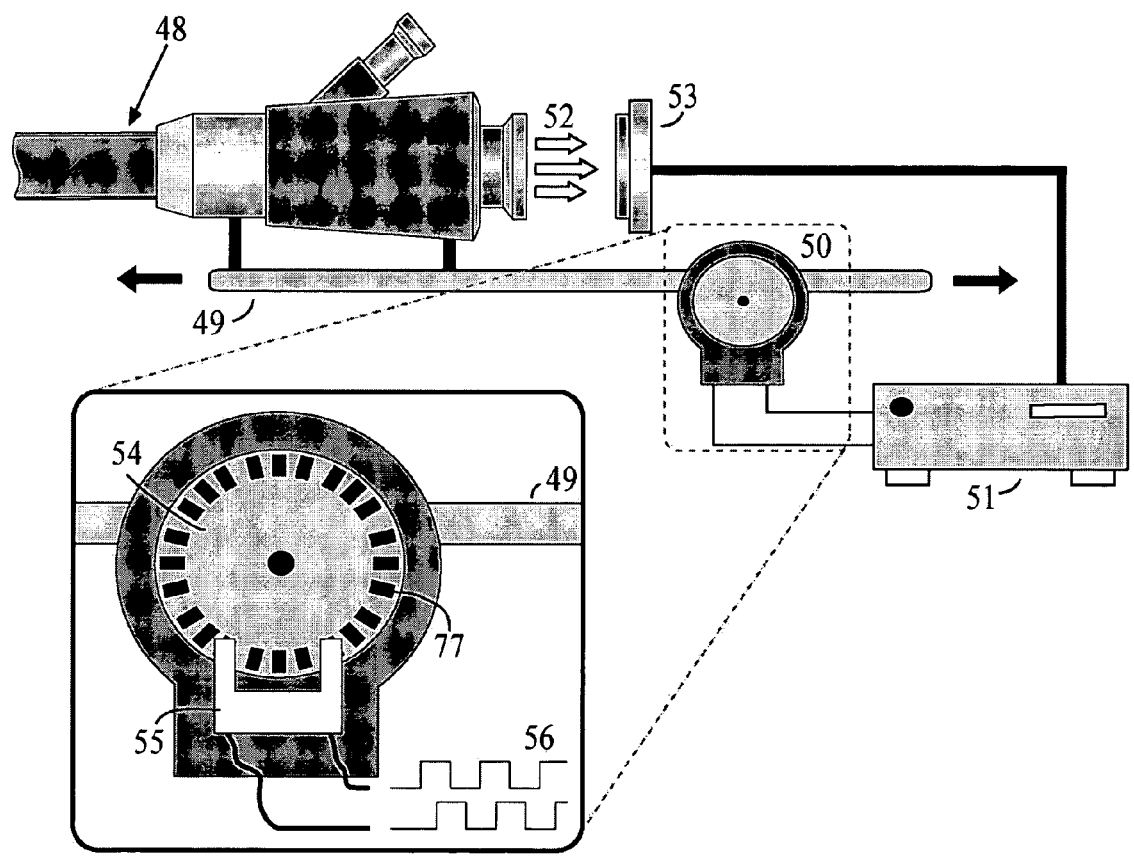
FIG. 9 shows a preferred embodiment of a position sensor apparatus. The endoscope (48) is attached to a linear track (49) with a bi-directional optical encoder (50). As the endoscope moves along the track, the optical encoder will detect changes in position. Therefore the position sensor controller (51) will know at what position the endoscope is at and trigger the detector (53) when the endoscope is at an established location.

A position sensor may synchronize with an imaging sensor such that images are captured at specific positions. This allows for fixed intervals between each image acquisition. One embodiment of an apparatus is shown and described in FIG. 9. FIG. 9 illustrates an endoscope (48) mounted on a linear track (49) so that it can be inserted and retracted along a single axis of motion. The motion of the endoscope (48) in either direction on the track is detected through an optical encoder (50) that is part of the embodiment. This optical encoder (50) is preferably bidirectional. The optical encoder (50) which is used with servomotors and robotic actuators, is able to detect changes in position. The optical encoder (50) is comprised of a round disk (54) with a number of holes (77) extending close to and around the outside edge of the disk and a pair of photo-diode detectors (55). As the endoscope moves along the track, the disk is spun by the motion. The pair of photo-diode detectors are mounted such that the disk (54) blocks the space between the diode and detector. When one of the holes (77) in the disk lines up with the photo-diode detector (55), the detector is able to detect the light from the photo-diode and outputs a signal. As the wheel turns, a pulse pattern is outputted (56) from the photo-diode detector that corresponds to the passing of each of the holes (77) in the disk. The holes (77) are preferably evenly distributed on the disk. As there are a known number of holes, the total distance that the wheel moved can be determined—which indicates the distance the endoscope moved. By using two of these photo-diode detectors, the sensor is able to detect the direction of the motion as well.

The position sensor controller (51) illustrated in FIG. 9 detects these changes from the signals that it is receiving from the optical encoder (56). Through this information, the controller has an accurate measure of any distance the endoscope traveled along the track. This allows the controller to trigger the detector (53) to capture the light (52) that is being imaged by the endoscope. This embodiment allows the device to know exactly how far apart each image in an image series was captured. Additionally, this allows the controller to set the position interval between each image captured.

The image series captured through the use of the apparatus contains visual distortions because of the omni-directional tip (either because of the mirror or the lens system). Each of the images has a characteristic 'fish-eye' distortion that needs to be corrected. Given that the distortion in the images is created by a known source (the lens or mirror at the endoscope tip), the distortion can be removed through software and image processing. This allows the device to collect together undistorted segments of the tissue and combines them into a single 2-dimensional map. This processing is accomplished through software after the image series has been acquired.

Figure 10:
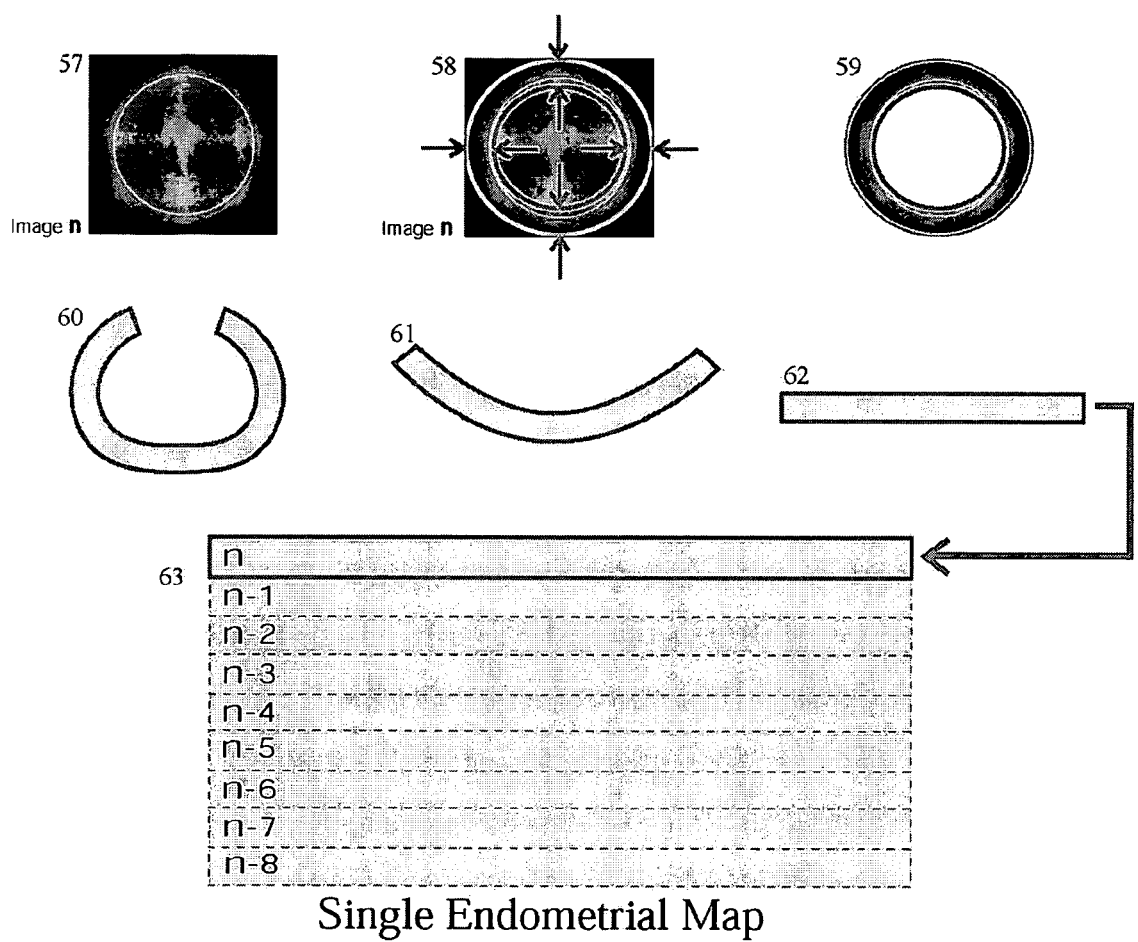
FIG. 10 shows an illustration of how an embodiment of the apparatus may process the images. The omni-directional image (57) is dewarped (60 to 62) and used to generate a single endometrial map (63).

FIG. 10 illustrates an example of the concept of dewarping the series of images. A single image (57) may contain 'fisheye' distortion because of the shape of the omni-directional viewing tip. In order to unwarp the image, a ring-like segment of the image is selected centered at the vanishing point in the middle of the image (58). The size or thickness of this ring is dependant on the distance the endoscope tip was moved between successive images and the resolution of the images.

Once the ring segment has been identified, the ring segment (59) is clipped out of the overall image for dewarping. Using a transformation based on the shape of the omni-directional viewing tip, the segment can be dewarped through steps (60, 61, 62) into a standard rectangular form (62). However, given that the thickness of the ring segment will preferably be small (in order to maintain high resolution in the endometrial map), in most embodiments, several segments from successive images (n, n-1, n-2, . . . ) will need to be combined or stacked together to form an overall single map (63). Therefore, as the image processing moves through the series of images, visual information about endometrial cavity is segmented out and the final endometrial map is built segment by segment. By taking advantage of the position sensor system (such as that illustrated in FIG. 8) and stacking the image segments one next to another (63), the apparatus is able to create an anatomically scale stack of ring segments (59). Therefore, the 'stacked' image contains anatomical information without the image warping seen in the initial image (57). Once through all the images in the image segment, a complete map has been generated, displaying the visual information that the apparatus collected in its procedure. The map may be of use to the physician, as it allows the user to see within the endometrial cavity or organ cavity and examine the tissue lining for areas of concern, polyps or other pathology.

Figure 11:
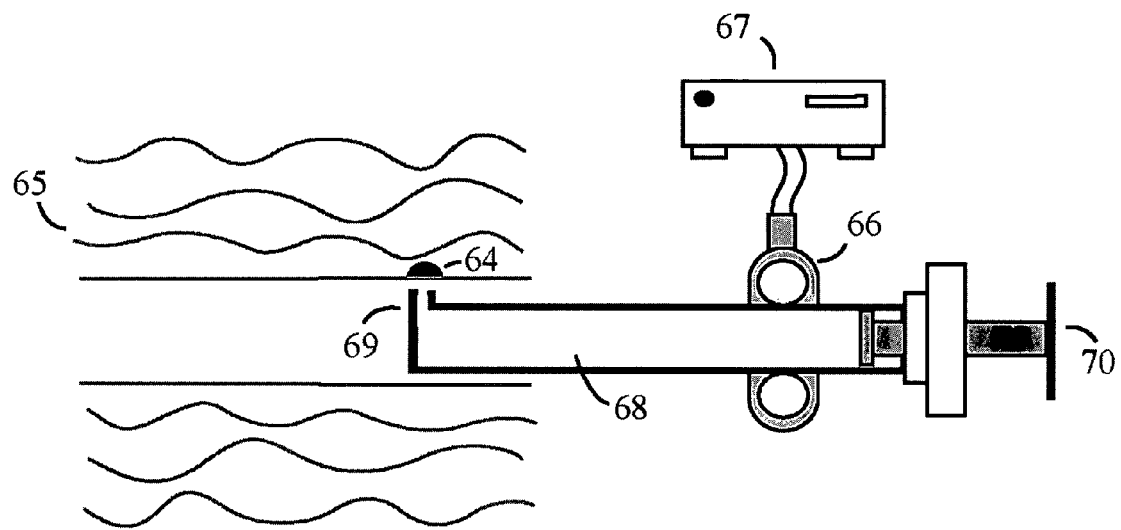
FIG. 11 shows an embodiment of a biopsy apparatus. Once an area of tissue has been identified by a clinician as being of concern (64), the same position sensory system (66, 67) can be used to position the biopsy apparatus to the area (64). Tissue samples will be gathered with the collector apparatus (69). Suction created by pulling the plunger back (70) will pull the tissue samples into the cylindrical lumen (68) within the device for histologic testing.

In another aspect of certain embodiments, a biopsy apparatus has the ability to be used in conjunction with the imaging apparatus. The technique for biopsy, whether it is performed through optical means (spectroscopy, optical coherence tomography, etc), or physical means, can be accomplished. An embodiment of physical biopsy is shown in FIG. 11. Once a clinician has identified an area of tissue, that area of concern (64) may be biopsied. Once the area of concern (64) in the region (65) has been identified through the use of the imaging apparatus, a positioning sensor system (66, 67) is able to use the same coordinate system used in the image processing algorithms and allow for the positioning of the biopsy apparatus over the area of concern (64). The embodiment uses the position sensor (66) and positioning controller (67) to position a collecting tip (69) at the area of concern (64). The tissue is scraped using the collection tip (69) to obtain a tissue sample. Suction is created within a cylindrical lumen (68) inside of the apparatus through the use of a plunger on the other end (70). The suction draws the sampled tissue into the lumen (68), where it is stored until the apparatus is retracted out of the body and the tissue can undergo histological analysis. Other methods for obtaining biopsy samples may also be utilized.

As set forth above, certain embodiments use and/or relate to an endoscope including an imaging channel and a tip positioned at one end of the imaging channel, the tip adapted to collect light from a field of view that extends 360° around at least a portion of the endoscope and to transmit the light to the imaging channel. Certain embodiments may also utilize various sensors, controllers and processing mechanisms to record and process images into a representation, move the endoscope in and out of the endometrial cavity, and to biopsy a portion of the endometrium. Other aspects and features described above may also be used in certain embodiments.

Aspects of certain preferred embodiments are also described in connection with FIG. 12, where to image the tissue within the endometrial cavity (or other organ) cavity (101), an endoscope system is used. As seen in the embodiment illustrated in FIG. 12, an imaging apparatus may include a rigid or flexible endoscope (102) with an illumination channel (103), and an imaging channel (104) for a camera, electrical transducer or other imaging technology that may be attached to the imaging channel (104) to capture images. In a preferred embodiment, the endoscope system may image with, but is not limited to, a tip (105) that it can allow it to visualize up to and including 360 degrees perpendicular to the optical axis of the endometrial cavity at a position in the endometrium at or adjacent to the tip (105). Other suitable tips may also be used. The endoscope is preferably positioned transcervically to the uterine fundus. As the apparatus is introduced or retracted, images of the endometrial cavity can be captured as the tip (105) of the scope passes through the cavity (101).

Figure 12:
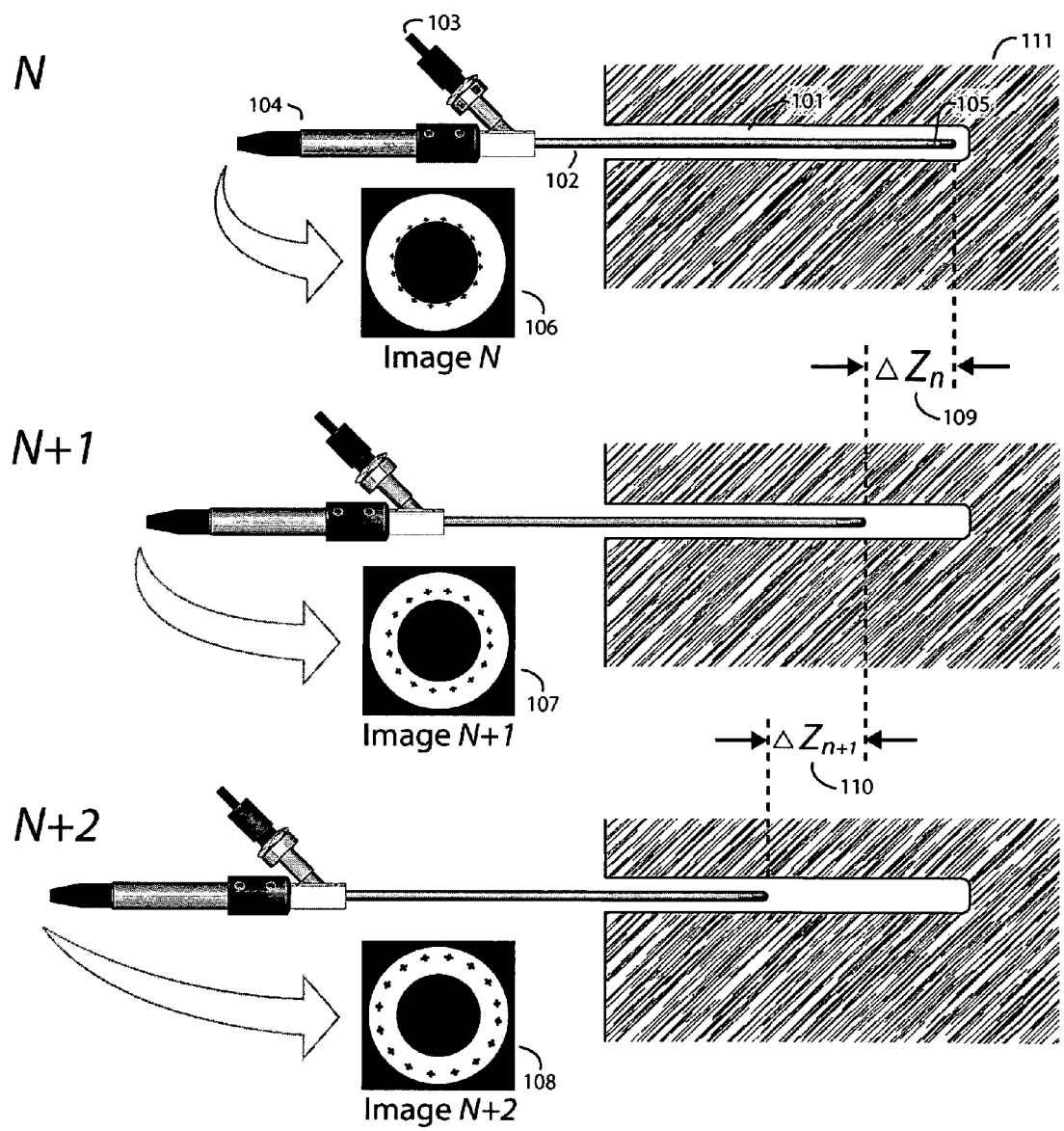
FIG. 12 is an illustration including an imaging system moving through a cavity in accordance with certain embodiments. As the system moves, the captured images will create an image series (Images 1, 2, 3, . . . M) of the field of view. A discrete motion will be captured between each image capture. In this embodiment, a displacement ($\Delta Z_n$) occurs between captures. However, other embodiments can contain more complex motion, including but not limited to rotation, scaling, deformation, patient motion, or motion caused by hand tremor.

As illustrated in FIG. 12, a change in the position of the endoscope (102) may result in a change in the position of the imaging tip (105) and the field of view. This may cause a change in how objects are oriented in the field and therefore the image geometry, or the relationship between objects in the captured image, may be altered by the motion. Examples of such motion include, but are not limited to, motion of the endoscope being inserted, retracted or moved laterally into the cavity, or the subject or patient moving with respect to the tip of the endoscope (105). As the endoscope moved through the cavity, images may be continually captured through the use of an imager at the imaging channel (104) which will generate an image series captured within the cavity. Discrete motion that occurs between images as the imaging system moves from one image capture to the next may cause changes in the field of view that is captured (107, 108, 109) in the image series and this information may be used to compute or model the discrete motion for the purposes of motion tracking. In the present embodiment, the motion between each image can be approximated, but is not limited to, four elements: translation, rotation, deformation, and scaling. The embodiment of the invention shown in FIG. 12 shows only translation motion (109, 110) between image captures for illustration purposes. Other components of inter-frame motion include, but are not limited to, rotation, deformation, and scaling.

As a portion of the imaging system, in accordance with certain embodiments, scans through the entire cavity, the change in the position of the system at each image acquisition can be captured in the image series. FIG. 13 illustrates one such preferred embodiment of an image series. Between each image in the illustrated series (204, 205, 206, 207) a discrete motion (201, 202, 203) may cause a change in the position of the endoscope in relation to the subject and therefore may cause a variation in the image geometry. By taking the whole image series or a subset of the image series (as illustrated in the case of the preferred embodiment shown in FIG. 13, four images are present), this embodiment of the invention will be able to use some or all the variations in image geometry within the images to calculate the intra-image motion. As described below, by tracking and measuring the inter-image motion, the present embodiment of the invention will allow for other functionality.

In certain embodiments of the invention, the imaging system may cause distortion in the images. Such distortion may be the result of the optical elements in some embodiments, or other components in other embodiments. One such distortion in certain embodiments may be 'fish-eye' distortion that may be caused by wide angle imaging elements in certain embodiments of the invention. While removing these distortions may not be necessary for certain embodiments in order to perform motion tracking methods, the performance of other imaging system embodiments may be improved by the removal of the distortion. In some embodiments, where imaging may be accomplished by imaging up to and including 360 degrees around at least part of a portion of the endoscope, the resulting 'fish-eye' distortion may be removed through the use of distortion removal methods. As illustrated in the embodiment shown in FIG. 3, each image that is captured through the imaging system (301) may contain 'fish-eye' distortion. Through the use of a distortion removal method (302), an image can be corrected of the distortion. In this embodiment, the resulting image (303) has been corrected into a rectangular format to remove the distortion. An undistorted or unwarped image, (as embodied in 303) can be included in the visual motion tracking methods described below.

Figure 15:
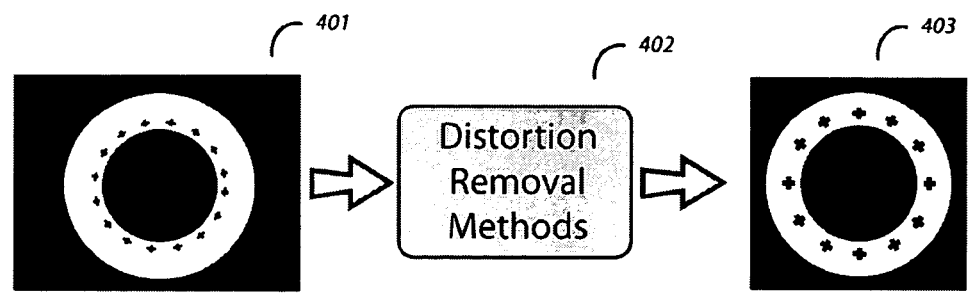
FIG. 15 illustrates distortion removal with images that are captured through the imaging system without unwarping in accordance with certain embodiments.

Because the image distortion may be related to the system's image formation geometry, the distortion removal methods may be implemented in different ways. FIG. 15 illustrates a different embodiment of a distortion removal method. In this embodiment, the captured image (401) is inputted into the distortion removal method (402), where the image distortion may be corrected. The resulting image (403), which in this embodiment retains its circular form, can be used in the visual motion tracking methods described below. In whichever embodiment the distortion removal is implemented in, by performing the removal method on each image within the image series or on a subset of the image series, the embodied imaging system has the option of removing the distortion for the images.

After at least two images have been acquired and optionally undergone distortion removal, certain embodiments of the invention will have the ability to calculate and/or model the motion that occurs between each image in the image series—the embodied system may perform visual motion tracking on images in order to determine the inter-frame motion that has occurred between image captures. Other embodiments of the invention that may be used to measure, model, or calculate the motion an imaging system may have undertaken between image captures includes, but is not limited to image processing on acquired images, physical frames, physical stages, contact trackers, optical trackers, electromagnetic trackers, non-contact trackers, and global positioning system trackers—said trackers may be used on either acquired images or during the process of image capture. FIG. 16 shows an embodiment of visual motion tracking using images that have been previously unwarped using an embodiment of distortion removal, as illustrated in FIG. 14. Two or more captured images (501, 502) from the image series or a subset of the image series can be used as part of the visual motion tracking method (503). Through computational methods, the changes in the images in the series can be detected, and an approximation or model of the inter-frame motion that occurred between the capture of the two or more images (501, 502) can be determined. The motion can be approximated and/or modeled by the visual motion tracking method (503) and can be embodied as a set of components. These components may include, but are not limited to: a translational component (504) which can include the direction and magnitude of the translation, a rotation component (505) which can include a direction and magnitude, a scaling component (506) which can include the magnitude of scaling, and a deformation component (507) which can contain model parameters or approximations that describe the deformation caused by the motion. These components, as a whole, can describe the motion, whether complex or simple, the imaging system underwent between image captures. It should be noted that embodiments of the invention other than those embodiments utilizing visual motion tracking methods (503) may be described in FIG. 16. In these embodiments, element (503) may be replaced by any other method for tracking or computing motion that may have occurred between images including, but not limited to image processing methods, methods utilizing physical frames and/or stages, methods utilizing contact sensors, methods using optical trackers, methods using electromagnetic trackers, methods using global positioning systems trackers, and methods utilizing other non-contact trackers.

Figure 17:
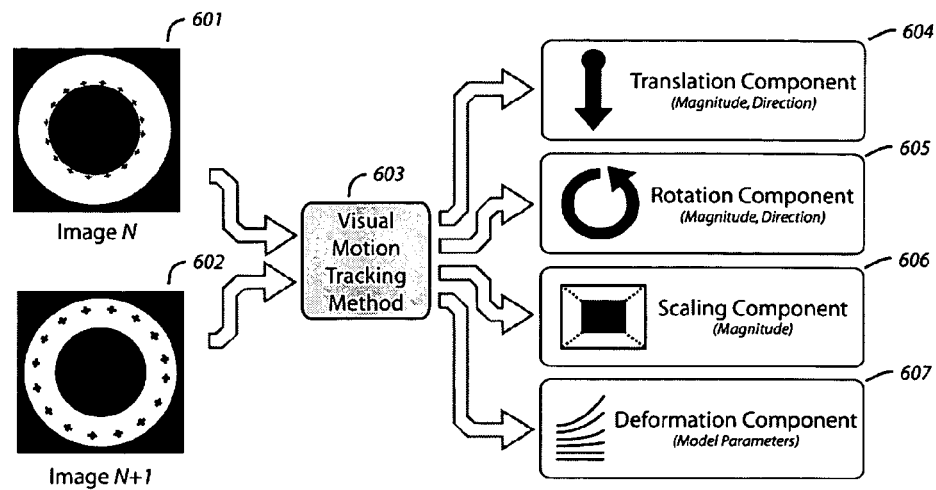
FIG. 17 illustrates a visual motion tracking system in accordance with certain embodiments. This system does not require any distortion removal or unwarping in order to perform motion tracking. The computation is performed on the captured images.

FIG. 17 demonstrates another embodiment of a visual motion tracking method. This method can utilize captured images that do not require any distortion removal and can be acquired directly from the imaging system. Two or more captured images (601, 602) from the image series or a subset of the image series can be used as part of this visual motion tracking embodiment (603). The visual motion tracking method, using but not limited to, software or computation methods, will approximate and/or model the inter-image motion as a set of components, similar to the embodied method in FIG. 16. These components may include, but are not limited to a translational component (604), a rotation component (605), a scaling component (606), and a deformation component (607). Through an embodiment of a visual motion tracking method, the motion of the imaging system between image captures can be determined by investigating the images in the image series or a subset of the image series. In a manner akin to FIG. 16, FIG. 17 may describe embodiments that may not utilize visual motion tracking methods (603). In these embodiments, element (603) may be replaced with any other method for tracking or computing motion that many have occurred between images including, but not limited to image processing methods, methods utilizing physical frames and/or stages, methods utilizing contact sensors, methods using optical trackers, methods using electromagnetic trackers, methods using global positioning systems trackers, and methods utilizing other non-contact trackers.

Figure 18:
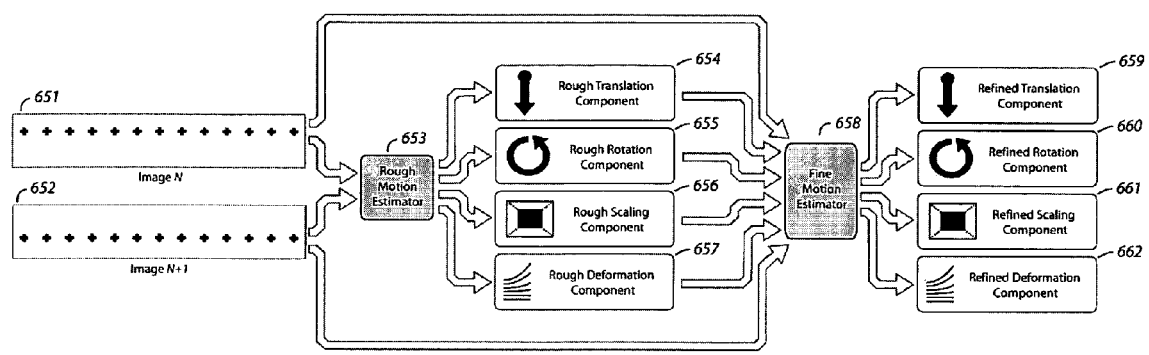
FIG. 18 illustrates a motion tracking method in accordance with certain embodiments. Using both a rough and fine motion estimator, the motion that occurred between images can be computed.

One preferred embodiment of a visual motion tracking method is to track the change and/or pattern in image pixel intensity between the two or more images being inputted. One embodiment of this method can be accomplished through the use of a gross motion estimator and/or a fine motion estimator as shown in FIG. 18. Initially, this method may start with one or more gross motion estimators (653), or a method that can estimate large motion between the inputted images (651, 652). Using a gross motion estimator, this method will allow the embodiment of the invention to estimate the large motion (illustrated by, but not limited to, the rough motion components 654-657) between two or more images. Following this, one or more methods for estimating small motion, such as a fine motion estimators (658), including, but not limited to an optical flow method, may use the rough motion components (654-657) to estimate small magnitude motion and be able to refine the motion estimation (illustrated by, but not limited to, the refined motion components 659-662). A preferred embodiment of a fine motion estimator is an optical flow method. In this embodiment of a fine motion estimator, by using some or all of the pixels within one or more of the images, the apparent motion between two or more images can be computed through image brightness patterns using an optical flow method. This fine motion estimator will improve the accuracy of the overall motion estimation. Using a combination of gross and fine motion estimators, whether one or the other or both, the visual motion tracking method can be used to calculate and track the motion that may have occurred between two captured images. Following the gross motion estimators, if needed, a brightness and/or contrast compensator may be optionally used on the images. This can compensate for fluctuations in the intensities of the images. An embodiment of a brightness and contrast compensator may be, but is not limited to a Laplacian of a Gaussian kernel filter, which is commonly used in image processing. However, if there are significantly small features within the images, the brightness and contrast compensators can be bypassed such that the features are not filtered out. By combining one or more gross motion estimators with one or more refined motion estimators, the motion computed between two or more images can be estimated with high accuracy.

Another embodiment of a visual motion tracking method can be described using individual features within the image and tracking these features between images. This method can be defined as feature based tracking. In this embodiment, the method may define and identify specific features within the images. Examples of such features include, but are not limited to, blood vessels, vasculature, or the texture of the tissue. By extracting one or more features from the image, all or a portion of these features can be identified through many if not all of the images in the image series. Once the features have been identified, the features can be tracked between images to determine the motion the image system underwent between captures. Any number of registration algorithms can be used with the feature-based method to track the features as they move through the image series. By tracking these features and registering their position from one image to another, the motion captured in the image series or subset of the image series can be modeled.

With the knowledge of the motion that has occurred between two or more images within an image series or a subset of the image series, this information may be used to combine or collage several images from the image series together into one or more constructed images. By knowing the motion parameters between images in the image series or subset of the image series, an embodiment of the invention can stitch two or more images together into a collaged image. An embodiment of the collaging algorithm can perform transformations to "line-up" the images and/or it can correct deformation in one or more images in the image series and/or fuse them into a single image or representation. The resulting image collage may allow a user of the embodiment of the invention to view the inner wall of a cavity by passing the endoscope through the cavity. By allowing the user of the embodiment of the invention to view the imaged tissue through the resulting representation the embodiment creates, the embodied representation may be used as a tool to identify or diagnose pathology within an organ system cavity. Certain embodiments of the present invention may utilized the combined representation or a portion of the representation as guidance for image guided procedures, such as but not limited to biopsy and therapy delivery.

FIG. 19 illustrates an embodiment of an image collaging method that can be used to combine two or more images or portions of two or more images together into at least one collaged image. To accomplish the embodied collaging method, the method can use the inter-image motion estimation determined using visual motion tracking methods. By inputting two or more images (701, 702), the embodiment of the invention can utilize the inter-image motion estimation components in the form of, but not limited to translation, rotation, scaling and deformation (703, 704, 705, 706), and determine how the images are registered to on another. Using this registration information or an embodiment of the registration information, the inputted images (701, 702) can be fused together (as shown in 708) into a collaged image or representation (709). By including or iterating through a series or subset of a series of images, the embodiment of the collaging method can build a resulting collaged image or representation (709) containing visual information or portions of visual information from some or all of the image in the series. As the images or portions of the images are fused into the image collage, a collaged image can continue to grow displaying more information captured in the image series or subset of the image series.

Another embodiment of the proposed invention can perform collaging on images that do not undergo any distortion removal. In a manner similar to FIG. 19, FIG. 20 illustrates an embodiment of image collaging with captured images that do not require distortion removal. Using two or more images (801, 802) and the motion components, including but not limited to translation (803), rotation (804), scaling (805), and deformation (806), the registration between the two or more images can be computed and the images or portions of the images can be fused together, through the use of an image collage method (807). The resulting collaged image or representation (808) can contain the information from all or portions of the inputted images (801, 802). Additionally this process can be iterated or include the image series or a subset of the image series to build a collage that contains some or all of the visual information within the image series or a subset of the image series.

Figure 21:
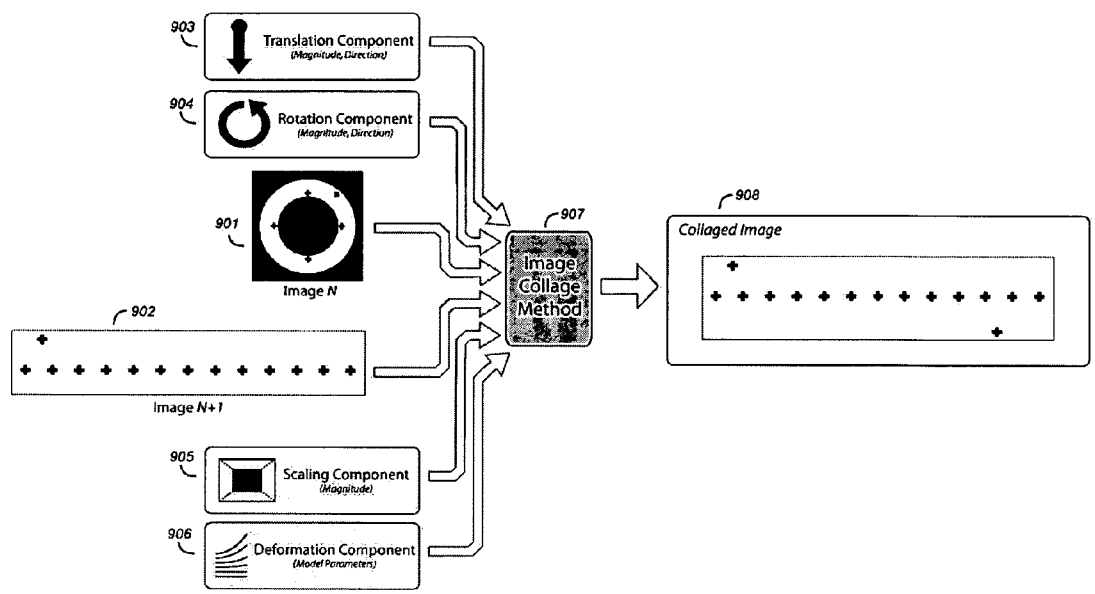
FIG. 21 illustrates an image collaging system in accordance with certain embodiments. This system utilizes multi-modal images.

Another embodiment of the proposed invention can perform collaging on images that may have been captured through different modalities. In such embodiments, the embodied system may create an image series or subset of an image series that contains images captures from difference modalities. These multi-modal image series or portions of the multi-model image series may be processed as any of the previously disclosed image series, including, but not limited to, determining any motion that may have occurred between multi-modal image captures image collaging process may In a manner similar to FIG. 19, FIG. 21 illustrates an embodiment of image collaging with captured multi-modal images. Using two or more images from a multi-modal image series or portions of a multi-modal image series, which may include but is not limited to, images captures with digital endoscopes, electrical transducers, or multi-spectral imaging devices, (901, 902) and the motion components, including but not limited to translation (903), rotation (904), scaling (905), and deformation (906), the registration between the two or more multi-modal images can be computed and the multi-modal images or portions of the images can be fused together, through the use of an image collage method (907). The resulting collaged image or representation (908) may contain the information from all or portions of the inputted multi-modal images (801, 802). Additionally this process can be iterated or include the multi-modal image series or a subset of the multi-modal image series to build a collage that contains some or all of the visual information within the multi-modal image series or a subset of the multi-modal image series.

It should be noted that some embodiments of the present invention may have the ability to track and/or compute at least two dimensional motion and/or features. As a result of this, the embodied system may compute representations of the captured image series or a subset of the capture image series that are at least two dimensions. One embodiment of the present invention may compute the three dimensional motion and/or features and collage or fuse the images together into a three dimensional representation or image. Another embodiment of the present invention may calculate the three dimensional features or the tissue or target object images in an image series or a subset of an image series, and build a three dimensional model representing the images tissue or target object. An example of such an embodiment may be, but not limited to, a mesh surface model, a triangle mesh surface model or a surface spline model. Additionally, embodiments of the present invention may integrate portions of the images from within the image series or a subset of the image series into the at least a two dimensional computed model to create at least a two dimensional or three dimensional representation that may give the appearance of the tissue or target object that was imaged. An example of such an embodiment may include, but is not limited to, displaying a portion of the image on the surface mesh elements (such as the triangle surface elements in a triangle surface mesh model).

It is, of course, understood that modifications of the present invention, in its various aspects, will be apparent to those skilled in the art. Additional method and device embodiments are possible, their specific features depending upon the particular application. For example, other data processing and representational methods may be used instead of or in addition to those discussed above. In addition, certain embodiments may be applicable to a variety of organ systems.

What is claimed:

1. A method for imaging an organ system cavity comprising:

positioning a first part of an imaging system in the organ system cavity;

acquiring a plurality of images using the imaging system, where the imaging system carries out imaging at angles up to and including 360 degrees around an axis of the first part of the imaging system;

removing distortion from the images by producing image segments from ring-like portions of each of the acquired images using a combination of clipping and dewarping processes that remove distortions introduced by imaging at angles up to and including 360 degrees around an axis of the first part of the imaging system;

combining at least portions of two or more image segments to create a map of at least a portion of the interior surface of the organ system cavity, wherein the combining at least portions of two or more image segments includes determining any motion of the first part of the imaging system relative to the organ system cavity;

wherein determining any motion of the first part of the imaging system is carried out using a visual tracking method that determines motion in the form of at least one motion component selected from the group consisting of translation, rotation, scaling, and deformation; and wherein at least one of the motion components is used to derive an image registration between two or more images that are used to create the map of at least a portion of the interior surface of the organ system cavity.

2. A method as in claim 1, wherein the organ system cavity comprises an endometrial cavity.

3. A method as in claim 1, wherein the organ system cavity is selected from the group consisting of or portions of a gastrointestinal lumen, an orthopedic joint cavity, a sinus cavity, a nasal passageway, an ear canal, an oral cavity, an intracranial space, a lung cavity, a bladder cavity, a cavity within the heart, a cavity within the vascular system, and at least a portion of the thoracic cavity.

4. A method as in claim 1, wherein the imaging system includes an endoscope, and at least a portion of the endoscope comprises the first part of the imaging system.

5. A method as in claim 4, wherein the endoscope is used to obtain the images and wherein the images are obtained without using insufflation of the organ system cavity.

6. A method as in claim 1, further comprising the use of a plurality of imaging modalities to obtain the at least portions of two or more of the images.

7. A method as in claim 6, where the plurality of imaging modalities are selected from the group consisting of digital cameras, digital endoscopes, stereo endoscopes, stereoscopic imaging systems, multi-spectral imaging systems, imaging systems utilizing electrical transducers, ultrasound imaging systems, nuclear medicine imaging systems, and x-ray imaging systems.

8. A method as in claim 1, further comprising determining the motion of the imaging device between the two or more of the images using at least one implementation selected from the group consisting of software, hardware, and firmware.

9. A method as in claim 1, wherein the images captured by the image system contain information about the tissue at a position selected from: (ii) on the surface of the organ system cavity, and (ii) below the surface of the organ system cavity.

10. A method as in claim 1, wherein the image of at least a portion of the interior surface of the organ system cavity is used to identify or diagnose pathology within or part of the organ system cavity.

11. A method as in claim 1, wherein the image of at least a portion of the interior surface of the organ system cavity is used as guidance in an image-guided procedure.

12. A method as in claim 11, wherein the image-guided procedure is selected from the group consisting of: (i) a biopsy, and (ii) the delivery of therapy or a portion of a therapy.

13. A method as in claim 1, wherein the visual motion tracking method includes the use of at least one of: (i) changes in image pixel intensity, and (ii) patterns in image pixel intensity, to determine the motion of the first part of the imaging system between the two or more images.

14. A method as in claim 13, wherein the visual motion tracking method includes the use of at least one estimator.

15. A method as in claim 14, wherein the at least one estimator includes a motion estimator that is implemented as a Kalman-type filter.

16. A method as in claim 14, wherein the at least one estimator includes a motion estimator that is implemented with an optical flow methodology.

17. A method as in claim 14, wherein the at least one estimator includes a motion estimator, the method further comprising using a compensator to adjust at least one of brightness and contrast, to improve image quality following the use of the motion estimator.

18. A method as in claim 17, where the compensator is implemented as a Laplacian of a Gaussian kernel filter.

19. A method as in claim 1, wherein the visual tracking method identifies features within a plurality of the images and tracks any change in orientation of the features due to motion of the first part of the imaging system between images.

20. A method as in claim 19, wherein the features comprise at least one feature selected from the group consisting of blood vessels, vascular structure, and tissue texture.

21. A method for imaging an organ system cavity comprising:
    positioning a first part of an imaging system within the organ system cavity;
    acquiring a plurality of images using the imaging system, the imaging system utilizing at least one electrical transducer to produce one or more images of a portion of the organ system cavity, where the imaging system carries out imaging at angles up to and including 360 decrees around an axis of the first part of the imaging system;
    removing distortion from the images by producing image segments from ring-like portions of each of the acquired images using a combination of clipping and dewarping processes that remove distortions introduced by imaging at angles up to and including 360 degrees around an axis of the first part of the imaging system;
    determining any motion of the first part of the imaging system relative to the organ system cavity; and
    combining at least a portion of two or more image segments into a map of at least a portion of the interior surface of the organ system cavity.

22. A method as in claim 21, wherein the acquiring a plurality of images includes using a light imaging system, wherein the light in the light imaging system is selected from the group consisting of ultraviolet light, visible light, near infrared light, and infrared light.

23. A method as in claim 21, wherein the electrical transducer is selected from a group consisting of an ultrasound sensor transducer, a radiation sensor transducer, and a nuclear medicine sensor transducer.

24. A method as in claim 21, where the at least a portion of two or more images includes images that were created or captured by at least two imaging modalities.

25. A method as in claim 21, wherein the image of at least a portion of the interior surface of the organ system cavity is used for the diagnosis or identification of pathology within or part of the organ system cavity.

26. A method as in claim 21, wherein the image of at least a portion of the interior surface of the organ system cavity is used as part of guidance for an image-guided procedure.

27. A method as in claim 26, wherein the image-guided procedure is selected from the group consisting of image-guided biopsy and image-guided therapy delivery.

28. A method as in claim 21, wherein the combining at least a portion of two or more images is accomplished as part of one of: (i) the acquiring a plurality of images, (ii) during the acquiring a plurality of images, or (iii) after the acquiring a plurality of images is completed.

29. A method as in claim 21, further comprising using the map of at least a portion of the interior surface of the organ system cavity to monitor time varying effects.

30. A method as in claim 21, wherein the combining at least a portion of two or more images removes at least one of noise and artifacts, in the captured images or portions of the captured images.

31. An imaging system comprising:
    an endoscope configured to image at angles up to and including 360 degrees around an axis of the endoscope;
    at least one image creating sensor configured to capture images from the endoscope;
    at least one data processing system; and
    at least one motion tracking system to determine motion between two or more images;

wherein the at least one data processing system is configured to remove distortion from the images captured from the endoscope by producing image segments from ring-like portions of each of the acquired images using a combination of clipping and dewarping processes that remove distortions introduced by imaging at angles up to and including 360 degrees around an axis of the endoscope; and wherein the at least one data processing system is adapted to combine at least a portion of two or more image segments together into a map of at least a portion of an organ system cavity.

32. An imaging system as in claim 31, comprising at least two image creating sensors, wherein the two image creating sensors are adapted to obtain at least two imaging modalities, and wherein the two or more images are acquired by the two imaging sensors.

33. An imaging system as in claim 31, further comprising a display device adapted to display at least a portion of the map of at least a portion of the organ system cavity.

34. An imaging system as in claim 31, wherein the imaging system is adapted to use at least a portion of the map of at least a portion of the organ system cavity as guidance for an image-guided procedure.

* * * * *